Figure 2:
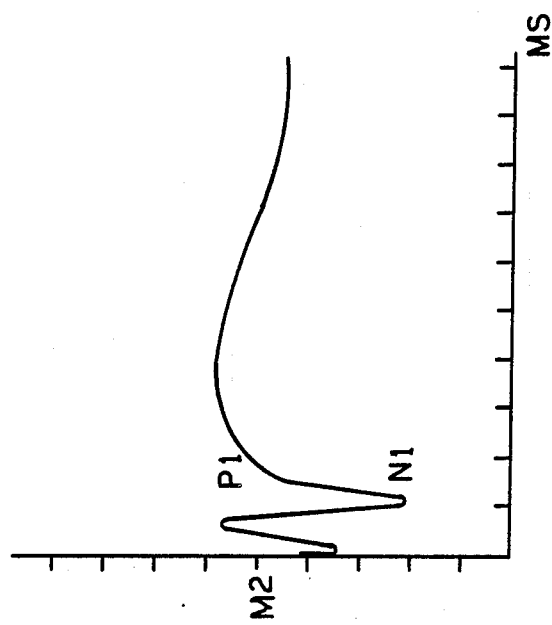

United States Patent [19]

Daniloff

[11] Patent Number: 4,955,892
[45] Date of Patent: Sep. 11, 1990

[54] NEURAL CELL ADHESION PROTEIN NERVE PROSTHESIS

[75] Inventor: Joanne K. Daniloff, Baton Rouge, La.

[73] Assignee: Louisiana State University, Baton Rouge, La.

[21] Appl. No.: 261,891

[22] Filed: Oct. 24, 1988

[51] Int. Cl.$^5$ ............................................. A61F 2/02
[52] U.S. Cl. ...................................... 606/152; 606/155; 623/12; 623/66; 424/423; 435/1; 514/2; 530/839
[58] Field of Search ...................... 623/12, 66; 435/1; 514/2; 530/839; 424/95, 108; 606/152, 154, 155

[56] References Cited

U.S. PATENT DOCUMENTS 4,662,884 5/1987 Stensaas .................................. 623/12

OTHER PUBLICATIONS

Seilheimer et al.; "Studies of Adhesion Molecules Mediating Interactions Between Cells of Peripheral Nervous System Indicate a Major Role for L1 in Mediating Sensory Neuron Growth on Schwann Cells in Culture", J. Cell Biol. 107(1) 1988, 341–352.

Joanne K. Daniloff, Giovanni Levi, Martin Grumet, Francois Rieger and Gerald M. Edelman, Altered Expression of Neuronal Cell Adhesion Molecules Induced by Nerve Injury and Repair, The Journal of Cell Biology, vol. 103, 9/86, pp. 929–945.

Gerald M. Edelman, Cell-Adhesion Molecules: A Molecular Basis for Animal Form, Scientific American, vol. 250, No. 4, Apr., 1984, pp. 118–129.

Primary Examiner—Alan W. Cannon
Attorney, Agent, or Firm—Llewellyn A. Proctor

[57] ABSTRACT

The neural cell adhesion molecule is used in nerve prostheses for the repair of peripheral nerve damage in mammals, both animal and man. In particular, in a process wherein a crushed or severed nerve ending is entubulated by use of a prosthetic device, a neural cell adhesion protein is added to the prosthetic device to increase the rate of growth of the fibrous components of the nerve, to more rapidly regenerate the nerve, and provide a more complete restitution of the function of the muscle served by the regenerated nerve.

14 Claims, 2 Drawing Sheets

NEURAL CELL ADHESION PROTEIN NERVE PROSTHESIS NOTICE OF FUNDING

This invention was made with government support under Grant No. NS25102-02 awarded by the National Institute of Health. The government may have certain rights in this invention.

FIELD OF THE INVENTION

This invention relates to a process for peripheral nerve repair to induce nerve regeneration in vertebrates. In particular, it relates to the use of neural cell adhesion protein for repairing damage in mammals, both animal and man.

BACKGROUND

After peripheral nerve damage, normal biochemical and morphological relationships between cell somata, their axonal and dendritic processes, and their terminations in targets such as muscle are disturbed both proximal and distal to the site of the injury. After a nerve is severed, the nerve end closest to the spinal cord normally begins to grow toward the other. The natural process of regeneration however is slow, and any number of things can obstruct or change the path of normal growth. One classical treatment for peripheral nerve repair requires "entubulization" of the severed nerve endings, a practice developed during World War II. In the practice of entubulization, empty plastic tubes are attached via microscopic sutures to the severed nerve endings; the tubes act as conduits to guide the growing nerve endings. Entubulization thus enhances the opportunity for some restitution of function, but unfortunately reverses only part of the damage. The restitution of function is rarely, if ever complete.

When a nerve link is broken the muscle which it serves begins to atrophy. The longer it takes for the nerve to regrow, the greater the damage to the muscle which it serves. Even after prosthetic implementation, considerable time is required and hence even after healing has begun, damage is sustained in the muscle served by the nerve. Consequently, the interaction of neuronal processes with the surfaces on which they grow has become a subject of increasing interest to neurobiologists interested in nerve regeneration. In vitro, it has been recognized that adhesion of growing processes, or neurites, to substrates is an important determinant of neurite elongation and that material deposited by non-neural cells can promote and direct neurite extension. Regenerating peripheral axons frequently grow along basal laminae (connective tissue) to reach and reinnervate their targets. These observations led to the demonstration that laminin, a glycoprotein which is a structural component of adult basal laminae, can promote some neurite outgrowth. Although other molecular substances have been found useful in promoting neurite outgrowth, most attention has focussed on laminin. See *Nature* Vol. 315, June 27, 1985, Pages 714–715 "Laminin for axonal guidance" Joshua R. Sanes.

OBJECTS

It is the primary objective of the present invention to provide improvements in the art of repairing damaged peripheral nerves in mammals, both animal and man.

In particular, it is an object to provide, in a process wherein severed peripheral nerve endings are held together by an implant device, an improvement which will increase the rate of growth of the fibrous components of the nerve, to more rapidly regenerate the nerve, and provide greater restitution of the function of the muscle served by the nerve.

A more specific objective is to provide improvements in the entubulation method of repairing damaged or severed peripheral nerves; improvements which will increase the rate of growth of the neural components of the nerve, to more rapidly regenerate it, and ultimately to provide greater restitution of the function of the muscle served by the nerve.

REFERENCE TO THE FIGURES

FIGS. 1 through 4 depict graphically the results of diagnostic tests (electromyography; or EMG), subsequently described in experimental animals.

Figure 1:
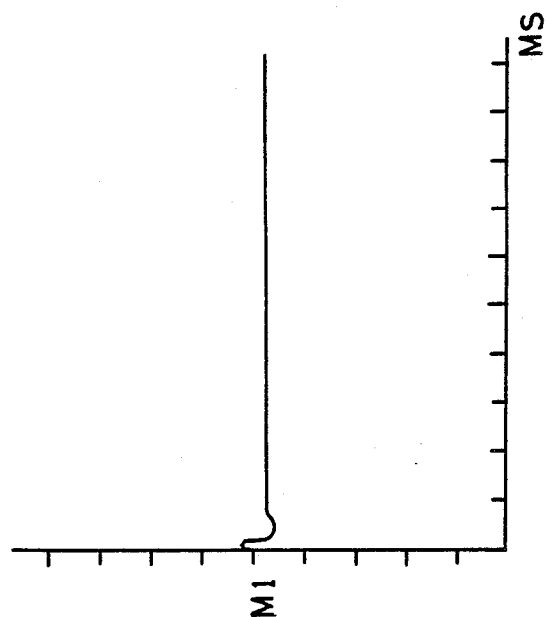

FIGS. 1 and 2 are controls that provide an EMG comparison between specific muscular response to an electrical stimulus. The N1 of each trace represents the speed at which each muscle responds to the current. This response is indicative of the general health of the nerve and, in normal nerves, is quite rapid (and measured in milliseconds). In FIG. 1 the left sciatic nerve has been severed and repaired via use of a conventional prosthetic entubulation device and a thirty day recovery period has occurred. The normal EMG response from the uninjured right leg is shown in FIG. 2.

Figure 3:
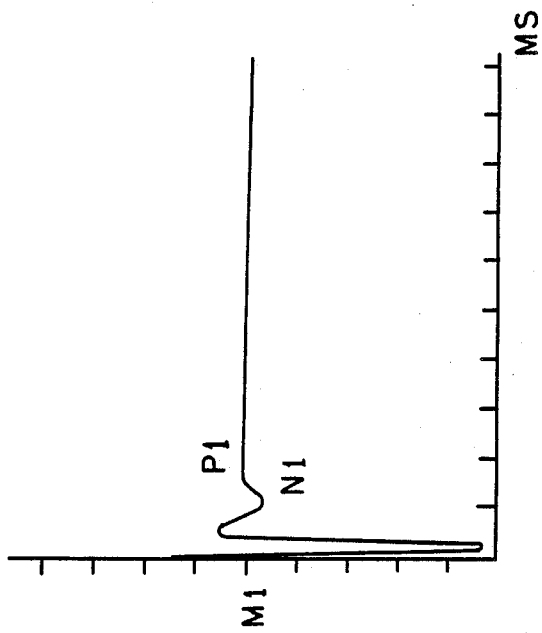
Figure 4:
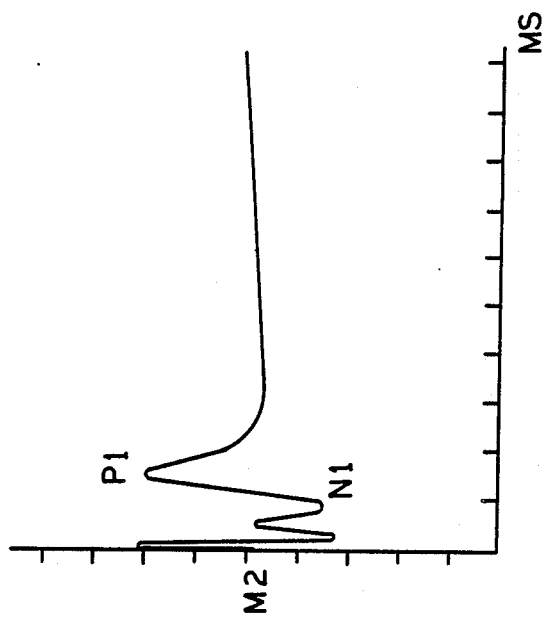

FIGS. 3 and 4 provide similar comparisons, except that the implant in the left leg of the second animal is impregnated with neural cell adhesion protein during the entubulization procedure.

THE INVENTION

These objects and others are achieved in accordance with this invention embodying, in a process wherein a severed nerve ending is directed toward the nerve ending from which it was severed by a prothesis device, or implant, the addition to the prosthetic device to which the proximate and distal ends of the nerve are directed, or joined, a molecular substance comprised of neural cell adhesion protein, preferably neural cell adhesion protein embedded in a semi-solid collagen matrix, sufficient to regenerate the fibrous components of the nerve causing them to grow rapidly. The rate of growth of the nerve fibers, and extent of regeneration of the nerve at the end of the period of regeneration is greater than can be achieved by the use of a prosthetic device otherwise similar except that neural cell adhesion protein is not added.

In conventional entubulation, empty plastic tubes are applied to the damaged nerves to guide the growth of the regenerating nerve ending. Entubulization enhances and provides some restitution of function which would not occur if the nerve gap were left unattended. The addition of neural cell adhesion protein, or neural cell adhesion molecules (hereafter N-CAM, or N-CAM protein), however, as required in the practice of this invention, will cause the fibrous components of the nerve endings to grow far more rapidly, more completely, with considerably greater, or more complete, restitution of the function of the affected muscle than possible with empty tubes, or tubes containing substances presently known for this purpose other than N-CAM. Thus, in treating nerve damage, the more rapid the rate of growth the more rapid the recovery of the nerve. Consequently the period of denervation of the affected muscle will be shortened, this allowing a more complete restitution of the function of the muscle than would occur under conditions where the rate of regeneration was slower.

The N-CAM that is applied in the treatment of a vertebrate species is preferably a purified N-CAM of the same species as that subjected to treatment. The N-CAM protein can be extracted from the brains of sacrificed vertebrates. Suitably, after extraction, the N-CAM is admixed with collagen. This gelatinous protein, the chief constituent of the fibrils of connective tissue and the bones, is found in all vertebrates. The N-CAM is admixed with the collagen generally in ratio of N-CAM collagen on a weight basis ranging from about 0.1:1 to about 10:1, preferably from about 0.4:1 to about 1:1. The N-CAM/collagen admixture, or N-CAM in the matrix of collagen, is added to a tube to which the proximate and distal ends of a nerve are joined. No immune system response has been found to occur in the treated vertebrate as a result of the N-CAM impregnated prosthesis for nerve regeneration.

The following non-limiting example is further illustrative of the invention, and specifically defines a preferred technique for obtaining the N-CAM, and the use of the N-CAM in nerve prosthesis.

In the example N-CAM was obtained from the brains of chicken embryos by extraction, the N-CAM recovered in high concentration and purified, the purified N-CAM embedded in a semi-solid collagen matrix (VITROGEN; Collagen Corp., Palo Alto CA), the N-CAM/collagen material added to a silastic tubing (Corning), the N-CAM/collagen tubing implanted in one of the legs of a first adult chicken, and attached to the nerve endings of the severed sciatic nerve of the animal by microsutures. An electric current was passed through the nerve thirty (30) days after the tube was implanted. The time it took for the muscle to begin to contract was used as a measure of nerve conduction velocity. A small number is indicative of a rapid response, as occurs in the healthiest nerves. N1, the entire contraction, was recorded, as was the peak of this response. The responsiveness of a target muscle to EMG is commonly used in sports medicine to determine the extent of damage and recovery of a muscle. Comparisons were made with the leg containing no implant. A matched control was run with a second chicken, one of its nerves having been injured and similarly entubulated. The control differed from the other runs only in that the use of N-CAM was omitted. Comparisons were made with the leg containing no implant; and with the test on the first animal.

EXAMPLE

A. Membranes containing N-CAM were first prepared from the brain tissue of embryonic chickens, to wit:
(1) Several brains of 13–14 day old chicken embryos were placed in beakers of 1X (1 Normal) phosphate buffered saline (PBS) on ice.
(2) Brains were removed and placed in a beaker of 1X calcium-magnesium free buffer (CMF).
3) The brains were homogenized, e.g., with manual mortar with pestle or polytron at #5 speed, 15 seconds, then again for 10 seconds. Use CMF with trasylol [protease inhibitor] with each homogenization. In advance make up about 200 ml CMF with about 8 ml trasylol.)
(4) Sucrose density gradients were made in an ultracentrifuge (Beckman Ti 45).

The bottom layer of the gradient tube consisted of about 2 ml of 42% sucrose in PBS.

The top layer, which contained the N-CAM, consisted of about 5 ml homogenate of about 10% sucrose content.

(To make 10% sucrose homogenate mixture, measure volume of homogenate and add 1/6 volume of 70% sucrose in distilled water. Add this mixture slowly to top of 42% sucrose bottom layer, tilt tube, and pour slowly on top.)

(5) The layer containing the N-CAM was added to tubes. The tubes were balanced and spun in Ti 45 rotor in ultracentrifuge for 30–60 minutes at 35 K (i.e., 35,000 RPM), 4° C.
(6) The membrane layers were poured into smaller tubes. (Approximately 6 membrane pellets per tube).
(7) The membranes were resuspended in cold PBS, and washed. (Fill tubes near full with buffer; membranes can be resuspended by beating with a spatula.)
(8) Tubes were balanced and spun in a GSA rotor in Sorvall centrifuge at 10K, 15–20 minutes, 4° C., to form a pellet with the membranes.
(9) The supernatant was discarded, the membrane pellets resuspended in cold PBS, and the PBS spun again at 10K, 15–20 minutes, 4° C. The volumetric size of the membrane pellets were measured. If 1× affinity purification occurred the following day, the membrane pellets were stored in a refrigerator with 1/100 volume of 1M $NaN_3$. If 1× affinity purification occurred the same day, the membrane pellets were simply stored as such in a freezer.

B. The N-CAM was separated from the membranes and purified via the following procedure, to wit:
(10) Fifty ml brain homogenates were extracted with an admixture of PBS/ NP 40 / EDTA (Nonidet P-40 (Sigma Chemical Company)/Ethylene diamine-tetraacetic acid Fisher Scientific) to remove the N-CAM from the homogenized brain tissue.
(11) The extract, containing the N-CAM, was next treated with beads to which N-CAM monoclonal antibodies (made by hybrid cloned cells produced in the laboratory and having an affinity for N-CAM) are attached, viz. Sepharose CL-2B beads (Pharmacea Fine Chemicals). A major amount of the N-CAM was taken up by the beads by adding the beads to a vessel containing the PBS/NP 40/EDTA and shaking for several hours on a rocking machine.
(12) The N-CAM was then eluted from the beads by contact of the beads with a salt solution (1 molar sodium chloride). The N-CAM was then concentrated by rapid dehydration and recovered.

C. Implant in one of the legs (the left) of each of two chickens of a prosthetic device, impregnation of one of the prosthetic devices with N-CAM, entubulization of the severed sciatic nerve endings with said prosthetic entubulization device, and comparative testing to determine the extent of regeneration of the damaged nerve, to wit:

Two young adult chickens (6 weeks of age) of identical species were anesthetized with choral hydrate, incision was made in a left leg of each and a sciatic nerve was cut equidistant to the greater trochanter and lateral condyle of the femur. This position was approximately equally spaced between the beginning of the lesioned nerve and its normal termination in the calf of the leg. A silastic tube (Corning) of 0.08 inches inner diameter (0.13 inches outer diameter) and 4 mm length was implanted in the cavities made by the incisions in the left leg in each animal. The opening within one of the tubes was filled with the N-CAM in admixture with sterile VITROGEN (Collagen Corp., Palo Alto, CA); sufficient to provide an admixtue of N-CAM:collagen in 2:3 ratio. The stumps of each sciatic nerve were microsutured to the ends of an implanted tube.

For electromyography, an electrical lead and electrode were placed above the proximal side of the sciatic nerve, or that side of the nerve connected to the central nervous system, and an electrical lead with a monopolar recording electrode and oscilloscope was inserted directly into the anesthetized animal's muscle (gastrocnemius). Similar connections were made in the same locations on the opposite, or right leg of each animal; having the normal sciatic nerve. An electrical current was passed through both the left and right legs of each of the animals thirty (30) days after implantation of the prosthetic devices and the current recorded. The results of these tests are graphically illustrated by reference to FIGS. 1-4.

FIGS. 1 and 2, respectively, are controls which demonstrate the muscular response obtained by contraction of the left leg of the first animal containing the implant to which no N-CAM had been added, and the normal right leg. FIGS. 3 and 4, respectively, demonstrate the results obtained between the left leg of the second animal containing the implant to which the N-CAM had been added, and the normal right leg of the animal. The x-axis of each graph is uniformly graduated in milliseconds, and the y-axis in terms of milliamps. Milliseconds are measured from the intersection of the x-y axis as "zero", positively to the right. The current is measured in milliamps from the x-y axis as "zero", positively when moving upwardly from zero. It is clear that in the left, or implant leg of the first animal after thirty days the amount of muscular contraction in response to the electrical stimulus is almost nil. However, in the normal right leg the time between initiation of the stimulus and initiation of the response, N1 is extremely rapid. The point of maximum response, P1, of the contracting muscle occurs within 2.56 milliseconds, i.e., [P1 (7.20 ms)-N1 (4.64 ms)=2.56 ms]. In striking contrast, the data show that the responsiveness of muscular contraction in the left leg of the second animal, or animal containing the N-CAM impregnated implant after thirty days of recovery is quite remarkable. The time between initiation of the response N1 and point of maximum response P1 is 2.40 milliseconds, viz., [P1 (6.08 ms)-N1 (3.68 ms)=2.40 ms]. The time of response of the normal right leg, in contrast, is 1.92 milliseconds [P1 (6.56 ms)N1 (4.64 ms)=1.92 ms]. Hence, the rapidity or rate of response of the injured left leg is 80% of that of the uninjured left leg after a period of only thirty days.

It is apparent that various changes and modification can be made as in the various sources of the N-CAM, the concentrations of N-CAM required for the treatment of various species and the like without departing the spirit and scope of the invention.

Having described the invention, what is claimed is:

1. In a process wherein the severed ends of the peripheral nerve of a living mammal, the function of which is to serve a muscle impaired by the break in the nerve, are directed via the use of an implanted prosthetic device to guide the proximate nerve end toward the distal nerve end to regenerate and repair the nerve the improvement comprising adding neural cell adhesion protein to the severed nerve ends held within said implanted prosthetic device sufficient to increase the rate of growth of the nerve vis-a-vis an implant device otherwise similar except that it does not contain said neural cell adhesion protein, to regenerate the nerve, and provide greater restitution of the muscle served by the nerve.

2. The process of claim 1 wherein the implanted prosthetic device is of tubular shape, the neural cell adhesion protein is added to the tubular opening therethrough, and to the proximate and distal nerve ends, respectively, are sutured to the ends thereof.

3. The process of claim 1 wherein the neural cell adhesion protein that is added to said implanted prosthetic device is admixed with collagen.

4. The process of claim 3 wherein the neural cell adhesion protein and collagen are admixed in weight ratio of neural cell adhesion protein: collagen ranging from about 0.1:1 to about 10:1.

5. The process of claim 4 wherein the neural cell adhesion protein and collagen are admixed in weight ratio of neural cell adhesion protein:collagen ranging from about 0.4:1 to about 1:1.

6. The process of claim 1 wherein the neural cell adhesion protein is obtained from a mammal of the same species as that in which the prosthetic device is implanted.

7. The process of claim 6 wherein the neural cell adhesion protein is obtained by extraction from the brains of a sacrificed animal.

8. The process of claim 7 wherein the neural cell adhesion protein is obtained by extraction from the brains of a sacrificed mammal of the same species as that in which the prosthetic device is implanted.

9. In a process wherein the severed ends of the peripheral nerve of a living human, the function of which is to serve a muscle impaired by the break in the nerve, are directed via the use of an implanted prosthetic device to guide the proximate nerve end toward the distal nerve end to regenerate and repair the nerve the improvement comprising adding neural cell adhesion protein to the severed nerve ends held within said implanted prosthetic device sufficient to increase the rate of growth of the nerve vis-a-vis an implant device otherwise similar except that it does not contain said neural cell adhesion protein, to regenerate the nerve, and provide greater restitution of the muscle served by the nerve.

10. The process of claim 9 wherein the implanted prosthetic device is of tubular shape, the neural cell adhesion protein is added to the tubular opening therethrough, and the proximate and distal nerve ends, respectively, are sutured to the ends thereof.

11. The process of claim 9 wherein the neural cell adhesion protein is added to said implanted prosthetic device is admixed with collagen.

12. The process of claim 11 wherein the neural cell adhesion protein and collagen are admixed in weight ratio of neural cell adhesion protein:collagen ranging from about 0.1:1 to about 10:1.

13. The process of claim 12 wherein the neural cell adhesion protein and collagen are admixed in weight ratio of neural cell adhesion protein:collagen ranging from about 0.4:1 to about 1:1.

14. The process of claim 9 wherein the neural cell adhesion protein is obtained from a human.

* * * * *